[19] United States Patent
Van Peppen et al.

[11] 4,200,553
[45] Apr. 29, 1980

[54] PROCESS FOR PRODUCING CYCLOHEXANONE

[75] Inventors: Jan F. Van Peppen; William B. Fisher, both of Chester, Va.

[73] Assignee: Allied Chemical Corporation, Morris Township, Morris County, N.J.

[21] Appl. No.: 951,551

[22] Filed: Oct. 16, 1978

Related U.S. Application Data

[63] Continuation-in-part of Ser. No. 827,189, Aug. 23, 1977, abandoned.

[51] Int. Cl.$^2$ .................. B01J 21/18; B01J 23/58; C07C 45/00
[52] U.S. Cl. .................... 252/447; 252/444; 260/586 P; 568/749
[58] Field of Search ................ 252/447, 444; 260/586 P

[56] References Cited

U.S. PATENT DOCUMENTS

| | | | |
|---|---|---|---|
| 2,692,240 | 10/1954 | Spraver | 252/412 |
| 2,760,940 | 8/1956 | Schwarzenbek | 252/466 |
| 2,777,805 | 1/1957 | Lefrancois et al. | 208/138 |
| 2,829,166 | 4/1958 | Joris et al. | 260/586 |
| 2,857,337 | 10/1958 | Hamilton | 252/447 |
| 2,857,432 | 10/1958 | Joris | 260/586 |
| 2,873,296 | 2/1959 | Nilson et al. | 260/586 |
| 3,076,810 | 2/1963 | Duggan et al. | 260/586 |
| 3,127,356 | 3/1964 | Hamilton, Jr. et al. | 252/447 |
| 3,187,050 | 6/1965 | Duggan et al. | 260/582 |
| 3,305,586 | 2/1967 | Phielix | 260/586 |
| 3,328,465 | 6/1967 | Spiegler | 260/575 |
| 3,542,863 | 11/1970 | Zimmershied | 260/525 |
| 3,692,845 | 9/1972 | Cheema et al. | 260/621 A |
| 3,959,382 | 5/1976 | Yeh et al. | 260/586 P |
| 3,965,187 | 6/1976 | Little et al. | 260/586 R |

FOREIGN PATENT DOCUMENTS

| | | |
|---|---|---|
| 892562 | 2/1972 | Canada . |
| 2163362 | 2/1972 | Fed. Rep. of Germany . |
| 2357370 | 5/1974 | Fed. Rep. of Germany . |
| 2619660 | 11/1976 | Fed. Rep. of Germany . |

*Primary Examiner*—P. E. Konopka
*Attorney, Agent, or Firm*—Richard A. Anderson

[57] ABSTRACT

In a process for producing cyclohexanone comprising hydrogenating phenol in the liquid phase in the presence of a catalyst composed of a carrier having deposited thereon a layer of palladium and an alkali metal compound as a promoter, the improvement wherein the carrier consists of carbon particles having diameters of 5 to 300 microns and the catalyst is admixed with 0.1 to 10 parts by weight, per part of catalyst, of carbon particles having diameters less than 5 microns. This improvement effectively reduces long-term accumulation of catalyst poisons on the catalyst, including catalyst poisons that are by-products of the hydrogenation reaction.

2 Claims, No Drawings

PROCESS FOR PRODUCING CYCLOHEXANONE

CROSS-REFERENCE TO RELATED APPLICATIONS

This application is a continuation-in-part of Application Ser. No. 827,189, filed Aug. 23, 1977 now abandoned.

This application is related to U.S. Applications Ser. No. 527,466 filed Nov. 26, 1974, now abandoned; Ser. No. 667,760 filed Mar. 17, 1976, pending; Ser. No. 667,735 filed Mar. 17, 1976, now abandoned; Ser. No. 793,563 filed May 4, 1977, issued as U.S. Pat. No. 4,092,360 on May 30, 1978; Ser. No. 886,718 filed Mar. 15, 1978, pending.

BACKGROUND OF THE INVENTION

This invention relates to the hydrogenation of phenol. More particularly, it relates to the hydrogenation of phenol to cyclohexanone in the presence of a promoted palladium catalyst.

In the hydrogenation of phenol employing a palladium catalyst, the activity of the catalyst, and hence the rate of hydrogenation, decreases with continued use of the catalyst due to impurities present in the hydrogenation reaction mixture which poison the catalyst. While processes, such as those disclosed in U.S. Pat. Nos. 3,692,845 and 3,187,050, have been developed to purify organic compounds such as phenol to be hydrogenated, the poisoning of metallic catalysts has not been entirely eliminated in large scale commercial processes due to long term accumulation of impurities, particularly impurities which are produced during the processing.

To avoid the economically prohibitive alternatives of discarding poisoned catalyst or continuing to use the poisoned catalyst at a reduced rate of hydrogenation, it is known to promote the rate of hydrogenation, thereby at least partially overcoming the disadvantages of continued use of such poisoned palladium catalysts. The hydrogenation of phenol to cyclohexanone is normally promoted by the use of "promoted palladium-on-carbon catalysts", i.e., catalysts which have been treated prior to their addition to the hydrogenation reaction mixture, to incorporate on the catalysts a material which enhances the activity of the catalyst. Thus, in U.S. Pat. No. 3,076,810, cyclohexanone is produced by hydrogenating phenol using a sodium-promoted palladium catalyst which has been modified prior to its introduction to the reaction mixture to incorporate sodium thereon. Alkaline reacting agents in limited amounts are also disclosed as being added to assist in promotion when the sodium-promoted catalysts are employed. However, such catalyst systems have not been entirely satisfactory because of long-term accumulation of catalyst poisons on the catalyst, and research has been continued to develop an improved process and/or catalyst.

Surprisingly, the process of present invention provides significantly improved catalyst selectivity and activity in the hydrogenation of phenol to cyclohexanone and mitigates long-term accumulation of catalyst poisons on the catalyst. Moreover, the improved catalyst and process minimizes the loss of palladium in commercial processes involving continuous hydrogenation of phenol. It is also important that the present process can be operated at a lower temperature than present commercial plants without sacrificing production rate.

SUMMARY OF THE INVENTION

The present invention may be summarized as follows: A process for producing cyclohexanone comprising hydrogenating phenol by passing hydrogen in contact with phenol in the presence of a palladium catalyst promoted by sodium in an amount of at least 1000 ppm, based on the weight of the catalyst, at a temperature of 135° C. to 185° C., preferably 145° C. to 175° C., said catalyst being further characterized in that it is composed of palladium coated carbon particles, said carbon particles having diameters of 5 to 300 microns and a surface area of 100 to 2000 m$^2$/gram, said catalyst being admixed with 0.1 to 10 parts by weight per part of catalyst of fine carbon particles having diameters less than 5 microns and a surface area of 100 to 5000 m$^2$/gram, said phenol containing a small amount of an in situ promoter selected from the group consisting of alkali metal hydroxides, carbonates and phenates, bicarbonates and nitrates, said amount being 10 to 300 ppm, preferably 15 to 150 ppm, in terms of alkali metal of said promoter.

It will be understood that the fine carbon particles may be admixed with the catalyst before or after the catalyst is added to the reaction mixture. Surprisingly, the fine carbon particles preferentially absorb catalyst poisons, e.g., tricyclohexylamine, phenylcyclohexylamine and dicyclohexylphenylamine, from the reaction mixture so that the palladium-on-carbon catalyst retains its high selectivity and activity over long periods of continuous operation.

By fine carbon is meant conventional porous carbonaceous material having vegetable or animal origin, and specifically excluding the oleophilic non-porous carbons prepared from hydrocarbon gases known as furnace blacks such as acetylene black, channel black, lamp black or furnace blacks. The palladium-free porous fine carbon of this invention preferably has a surface area of 200 to 5,000 m$^2$/gram.

Although in U.S. Pat. No. 3,076,810, it was said that higher concentrations, i.e., more than 10 ppm, of an alkaline reacting compound in the phenol favored the formation of cyclohexanol, we have found that in the presence of our improved palladium-on-carbon catalyst, not only is the reaction rate enhanced but also the production of cyclohexanol is reduced by operating within the range of 10 to 300 ppm of alkali metal in the phenol.

The palladium catalysts useful in the present invention contain palladium in either its elemental or combined form. Preferably, at least 30 to 75 percent of the total palladium is present as elemental palladium, i.e., as palladium zero. The palladium is desirably absorbed or coated on the surface of a support consisting of carbon particles, said carbon particles having diameters of 5 to 300 microns and a surface area of 100 to 2000 m$^2$/gram. It is preferred that the catalyst have at least 85 weight percent of the particles between 5 and 150 microns in diameter. While the amount of palladium incorporated on the selected support may vary widely, the catalyst preferably contains from about 0.2 to 10 weight percent palladium. A satisfactory and readily prepared catalyst contains 0.5 to 5 weight percent palladium on charcoal. In addition, the palladium catalysts useful in the present invention may contain catalytically active metals in addition to palladium. Such additional catalytically active metals which may be employed are those selected from the group consisting of elements of the platinum series. Exemplary of platinum series elements which may be employed are ruthenium, rhodium, osmium, iridium, platinum and mixtures thereof.

The preferred in situ promoters of the present invention are selected from the group consisting of sodium hydroxide, sodium carbonate, sodium phenate, and mixtures thereof. Particularly preferred as promoters in the present invention are sodium hydroxide and sodium phenate. The selected promoter may be added to the hydrogenation reaction mixture as a phenol slurry containing up to about 25 weight percent, and preferably from about 1 to 10 weight percent, of the selected promoter. Alternatively, the promoter may be added to the hydrogenation reaction mixture as an aqueous solution.

The phenol which may be employed in the present invention may be obtained from conventional sources, such as by the oxidation of cumene to form cumene hydroperoxide and the decomposition of the resulting hydroperoxide. However, the phenol treated in accordance with the process of the present invention will generally contain no more than about 100 ppm sulfur impurities, and preferably not greater than about 10 ppm sulfur impurities containing divalent sulfur, not greater than about 20 ppm sulfur impurities containing tetravalent sulfur and not greater than about 80 ppm, and most preferably not greater than about 40 ppm, sulfur impurities containing hexavalent sulfur.

The phenol also preferably contains not greater than 2 ppm, and most preferably not greater than 1 ppm, iron values (calculated as elemental iron); and preferably not greater than 100 ppm, and most preferably not greater than 50 ppm, acetol (i.e., hydroxy-2-propanone).

The phenol hydrogenated in accordance with the process of the present invention may also contain a wide variety of other impurities. These impurities include, for example; halogen compounds and deleterious nitrogen compounds, i.e., nitrogen-containing compounds which inhibit the hydrogenation of phenol to cyclohexanone employing palladium catalysts. Typical deleterious nitrogen compounds include aromatic amines, ammonium salts, polyamines, and tertiary and primary amines. Preferably, the phenol contains less than 10 ppm halogen and less than 50 ppm of nitrogen as deleterious nitrogen compounds. Continuous or batch techniques can be used in this improved process for hydrogenating phenol to cyclohexanone, the equipment used being that which is usual in such processes.

The selected in situ promoter may be introduced to the hydrogenation reaction mixture either prior to hydrogenation or during hydrogenation. Thus, the conditions of temperature under which the promoter may be added to the hydrogenation mixture are not critical and may vary widely. For example, the temperature at which the promoter is added to the hydrogenation reaction mixture may vary from about 25° C. to about 185° C. and the pressure may vary from about atmospheric to 300 psig. While an improved rate of hydrogenation is generally observed immediately upon addition to the hydrogenation reaction mixture of a promoter of the present invention, even more improved results may be obtained where the hydrogenation reaction mixture is maintained at a temperature within the range of about 135° C. to 185° C. and a pressure of 80 to 200 psig. for a period of 15 to 30 minutes after addition thereto of the selected promoter.

The selected in situ promoter may be added to the hydrogenation reaction mixture and the reaction product may be withdrawn from the hydrogenation vessel either continuously or batchwise. Upon withdrawal of the hydrogenation product from the reaction vessel, the palladium catalyst may be recovered from the product stream and returned to the vessel for hydrogenation of additional phenol. The recovery of the catalyst from the product stream may be effected by any standard solids separation procedure, e.g., centrifugation, vacuum filtering, and the like.

Vessels which may be employed during the hydrogenation are conventional, and include the typical hydrogenation apparatus such as, for example, the apparatus described in U.S. Pat. No. 3,076,810.

DESCRIPTION OF THE PREFERRED EMBODIMENT

The present invention is further illustrated by reference to the following examples wherein parts and percentages are by weight unless otherwise indicated. The improved catalyst and the improved rates of hydrogenation achieved by the process of the present invention are especially significant in view of the large tonnages of palladium catalysts used annually by industry in the hydrogenation of phenol to cyclohexanone. Furthermore, the in situ promoters of the present invention have been unexpectedly found to promote the hydrogenation of phenol to cyclohexanone while appreciably decreasing the amount of cyclohexanol produced by the further hydrogenation of the desired cyclohexanone hydrogenation product. Thus, recovery of cyclohexanone from the hydrogenation product stream, as by distillation, is not further complicated by the formation of substantial amounts of undesired products, i.e., cyclohexanol.

EXAMPLE 1

This example demonstrates the feasibility of continuously operating the hydrogenation process of the present invention. The phenol used has a purity of at least 99.8 percent and contains less than 1 ppm of soluble iron, less than 2 ppm of sulfur, less than 5 ppm of halogen, and 30–35 ppm of nitrogen as deleterious nitrogen compounds, i.e., nitrogen-containing compounds which inhibit the hydrogenation of phenol to cyclohexanone, as discussed hereinabove.

The first of a series of five agitated hydrogenation vessels is charged with 45,700 parts per hour of phenol, 1.3 to 2.0 parts per hour of sodium hydroxide, and 120 parts per hour of fine carbon particles having diameters between 0.1 and 5 microns and a surface area of about 1500 $m^2$/gram, admixed with 1200 parts per hour of a sodium-promoted, palladium-on-carbon catalyst having a sodium content of 0.35 percent, said catalyst containing about 0.9 percent palladium-on-carbon particles having diameters of about 5 to 150 microns and a surface area of about 1000 $m^2$/gram. About 67 percent of the palladium on the catalyst is present as elemental palladium. Each hydrogenation vessel is connected in series so that the reaction mixture flows through the five vessels in about 3 hours, excess hydrogen being charged to the first vessel. From each of the vessels, unreacted hydrogen is passed through a condenser for separation of crude cyclohexanone before the hydrogen is passed to the following vessel or recycled in the process. The pressure is between 80 and 200 psig. The temperature in each vessel is as follows: 173° C. in the first vessel; 166° C. in the second vessel; 162° C. in third vessel; 159° C. in the fourth vessel, and 156° C. in the fifth vessel. It is noteworthy for reasons of safety that the temperature in each vessel is less than the atmospheric boiling point of the reaction mixture present in the vessel. About 24,750 parts per hour of distillate, primarily cyclohexanone, is separated from the last four vessels; this distillate is rectified to provide substantially pure cyclohexanone. Distillate from the first vessel is preferably fed to the second vessel. The reaction mass flowing from the fifth reaction vessel is fed to a continuous centrifuge, wherein the catalyst is separated from the crude cyclohexanone; the recovered catalyst is recycled in the process. It is important that the fine carbon particles having diameters less than 5 microns remain in the crude cyclohexanone because the deleterious nitrogen compounds and other catalyst poisons preferentially absorbed on said fine carbon particles are separated from the catalyst which is recycled in the process. The crude cyclohexanone is rectified to recover substantially pure cyclohexanone which may be combined with the cyclohexanone recovered as described above.

In this example, average yield of cyclohexanone over a one-month test period is 98 percent of theory based on phenol fed to the process. Cyclohexanol is produced at a very low rate of about 610 parts per hour. At the end of the test period, the recycling catalyst contains about 0.45 percent sodium and about 0.9 percent palladium. A sample of the recycling catalyst showed no build up of deleterious nitrogen compounds. However, in a similar test wherein no fine carbon particles were admixed with the catalyst, there was a significant build up of deleterious nitrogen compounds on the catalyst.

EXAMPLE 2

The procedure of Example 1 is repeated with the exception that 1.6 parts per hour of sodium carbonate is added to the reaction mixture in place of the sodium hydroxide. Results obtained are similar to those obtained in Example 1.

EXAMPLE 3

The procedure of Example 1 is repeated with the exception that 2 parts per hour of sodium phenate is added to the reaction mixture in place of the sodium hydroxide. Results obtained are similar to those obtained in Example 1.

EXAMPLE 4

This example demonstrates one effective method of preparing a catalyst suitable for use in Example 1. It will be understood that this catalyst must be admixed with fine carbon particles in accordance with the process of this invention.

About 150 parts of commercially available charcoal catalyst support having particle size distribution of 30 percent less than 10 microns, 67 percent in the range 10 to 100 microns, and 3 percent greater than 100 microns is thoroughly mixed with 1850 parts of cyclohexanone, and this mixture is passed through a continuous centrifuge which operates at 3800 revolutions per minute. By this procedure, part of the charcoal particles consisting of the finer particles, passes out of the centrifuge with the cyclohexanone. The larger charcoal particles collected in the centrifuge, after drying, consist substantially of particles having diameters of 10 to 100 microns and a surface area of about 1000 $m^2$/gram. To 100 parts of said larger charcoal particles is added 1000 parts of aqueous palladium chloride solution containing 5 parts palladium and 3 parts hydrochloric acid. The resulting mixture is gradually neutralized with a sodium carbonate solution up to pH=1.5. The mixture is stirred and then filtered. The separate solids ae dried at 100° C. for 8 hours following which they are impregnated with 80 parts of a solution containing 5 parts of sodium carbonate, then dried at 100° C. to 120° C. The resulting catalyst is preferably reduced with a stream of hydrogen at 140° C. to 400° C.

We claim:

1. A process for preparing a modified catalyst for selective hydrogenation of phenol to cyclohexanone which comprises: (a) providing a sodium promoted palladium catalyst containing 0.2 to 10 weight percent of palladium, based on the total weight of said catalyst, said catalyst being supported on carbon particles having a surface area of 100 to 2000 $m^2$/gram, wherein substantially all of said particles have diameters of 5 to 300 microns; and (b) admixing said sodium promoted palladium catalyst with 0.1 to 10 parts by weight per part of said sodium promoted palladium catalyst, of fine carbon particles having diameters less than 5 microns and a surface area of 200 to 5000 $m^2$/gram, said particles being conventional porous carbonaceous material having vegetable or animal origin.

2. A modified catalyst for selective hydrogenation of phenol to cyclohexanone which consists of: (a) a sodium promoted palladium catalyst containing 0.2 to 10 weight percent of palladium and at least 1000 ppm sodium, based on the total weight of said catalyst, said catalyst being supported on carbon particles having a surface area of 100 to 2,000 $m^2$/gram, wherein substantially all of said particles have diameters of 5 to 300 microns; and (b) 0.1 to 10 parts by weight per part of said sodium promoted palladium catalyst, of fine carbon particles having diameters less than 5 microns and a surface area of 200 to 5000 $m^2$/gram, said particles being conventional porous carbonaceous material having vegetable or animal origin.

* * * * *